United States Patent
Hois et al.

[11] Patent Number: 6,153,762
[45] Date of Patent: Nov. 28, 2000

[54] BRIDGED BIS-4,5-DIHYDROXYIMIDAZOLIDIN-2-ONES, N-METHYLOLATED DERIVATIVES THEREOF, THEIR PREPARATION AND CROSSLINKING TEXTILES THEREWITH

[75] Inventors: Pia Hois, Birkenau; Jürgen Reichert, Limburgerhof, both of Germany

[73] Assignee: BASF Aktiengesellschaft, Ludwigshafen, Germany

[21] Appl. No.: 09/147,633

[22] PCT Filed: Jul. 31, 1997

[86] PCT No.: PCT/EP97/04171

§ 371 Date: Feb. 5, 1999

§ 102(e) Date: Feb. 5, 1999

[87] PCT Pub. No.: WO98/05650

PCT Pub. Date: Feb. 12, 1998

[30] Foreign Application Priority Data

Aug. 5, 1996 [DE] Germany ............ 196 31 618

[51] Int. Cl.⁷ .................. C07D 403/12; D06M 13/322
[52] U.S. Cl. ................... 548/313.7; 548/314.1; 8/189
[58] Field of Search ............ 548/314.1, 313.7; 8/189

[56] References Cited

U.S. PATENT DOCUMENTS

| | | | |
|---|---|---|---|
| 3,652,583 | 3/1972 | Tajima et al. | 548/314.1 X |
| 3,890,095 | 6/1975 | Bann et al. | 8/185 |
| 4,284,536 | 8/1981 | Bezwada | 548/314.1 X |
| 4,298,747 | 11/1981 | Frick et al. | 548/314.1 |
| 4,306,872 | 12/1981 | Herbes et al. | 8/189 |

FOREIGN PATENT DOCUMENTS 0762344 11/1956 United Kingdom.
1170012 11/1969 United Kingdom.

OTHER PUBLICATIONS

Niebergall et al, Chemical Abstracts, vol. 78, #5 44433h and 44433j, 1973.

*Primary Examiner*—Floyd D. Higel
*Attorney, Agent, or Firm*—Oblon, Spivak, McClelland, Maier & Neustadt, P.C.

[57] ABSTRACT

Bridged, methylolated bis-4,5-dihydroxyimidazolidin-2-ones conforming to the formula 1

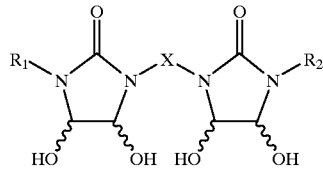

(1)

where $X=(CH_2)_n$ where n=2, 3, 4, 5, 7, 8, 9 or 10, branched or cyclic alkyl, each with or without hetero atoms such as O, S, N, P in the alkyl chain,
$CH_2CH_2(-OCH_2CH_2)_m$,
$CH_2CH_2CH_2(-OCH_2CH_2CH_2)_m$,
$CH_2CH_2CH_2(-OCH_2CH_2)_mOCH_2CH_2CH_2$,
$CH_2CH_2(-OCH_2CH_2CH_2)_mOCH_2CH_2$,
$CH_2CH_2CH_2CH_2(-OCH_2CH_2CH_2CH_2)_m$,
$CH_2C(CH_3)H(-OCH_2C(CH_3)H)_m$ or
$CH_2CH_2CH_2(-OCH_2CH_2CH_2CH_2)_mOCH_2CH_2CH_2$,
where m=0–7,
and
$R^1,R^2=H$ and/or $CH_2OH$, are prepared in one or two stages, the one-stage process also providing those where $X=(CH_2)_6$, and are useful in textile finishing.

11 Claims, No Drawings

BRIDGED BIS-4,5-DIHYDROXYIMIDAZOLIDIN-2-ONES, N-METHYLOLATED DERIVATIVES THEREOF, THEIR PREPARATION AND CROSSLINKING TEXTILES THEREWITH

This application is a 371 of PCT/EP97/04171 filed Jul. 31, 1997.

BACKGROUND OF THE INVENTION

1. Field of the Invention

The present invention relates to bridged methylolated bis-4,5-dihydroxyimidazolidin-2-ones, conforming to the formula 1

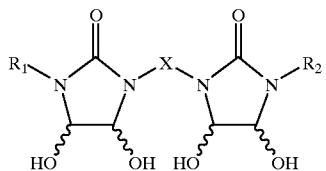

(1)

where $X=(CH_2)_n$ where n=2, 3, 4, 5, 7, 8, 9 or 10, branched or cyclic alkyl, each with or without hetero atoms such as O,
S, N, P in the alkyl chain,
$CH_2CH_2(-OCH_2CH_2)_m$,
$CH_2CH_2CH_2(-OCH_2CH_2CH_2)_m$,
$CH_2CH_2CH_2(-OCH_2CH_2)_m OCH_2CH_2CH_2$),
$CH_2CH_2(-OCH_2CH_2CH_2)_m OCH_2CH_2$,
$CH_2CH_2CH_2CH_2(-OCH_2CH_2CH_2CH_2)_m$,
$CH_2C(CH_3)H(-OCH_2C(CH_3)H)_m$ or
$CH_2CH_2CH_2(-OCH_2CH_2CH_2CH_2)_m OCH_2CH_2CH_2$,
where m=0–7,
and
$R^1,R^2$=H and/or $CH_2OH$, to a process for preparing them and to their use in textile finishing, especially on cellulosics.

2. Description of the Background 4,5-Dihydroxy-1,3-dimethylolimidazolidin-2-ones are used as formaldehydic crosslinkers in textile finishing. They impart good crease recovery and reduce textile shrinkage. However, the strength of the fabric is greatly impaired. In addition, the use of these substances on textiles leads to elevated formaldehyde values, which are no longer acceptable to most users for ecotoxicological reasons.

Food chemists use certain crosslinkers to control the gas permeability of cellophane. The compounds of the general formula 1 where $X=(CH_2)_6$ and $(CH_2)_{12}$ are described by H. Niebergall and H. Seitz in Angew. Makromolekulare Chem. 21 (1972) 41–51; ibid 113 to 128; and ibid 129 to 142. These compounds are, as stated, suitable for crosslinking cellophane and especially for controlling the gas permeability. They are prepared in a two-stage process in which the corresponding bridged urea derivative and glycol are first reacted to prepare the corresponding bridged imidazolidin-2-one. In the second stage, the bridged imidazolidin-2-one is reacted with formaldehyde to form the corresponding hydroxymethylated compound. Nowhere in the literature is there any mention of the use of these known compounds in textile finishing.

SUMMARY OF THE INVENTION

It is an object of the present invention to provide textile crosslinkers which provide good crease recovery and shrinkage reduction without significantly impairing the strength of the fabric. In addition, their use on textiles shall not raise the formaldehyde value to an ecologically unsafe level.

DETAILED DESCRIPTION OF THE PREFERRED EMBODIMENTS

We have found that this object is achieved by bridged, if appropriate methylolated bis-4,5-dihydroxyimidazolidin-2-ones conforming to the formula 1 where $X=(CH_2)_n$ where n=2, 3, 4, 5, 7, 8, 9 or 10, branched or cyclic alkyl, each with or without hetero atoms such as O, S, N, P in the alkyl chain,
$CH_2CH_2(-OCH_2CH_2)_m$,
$CH_2CH_2CH_2(-OCH_2CH_2CH_2)_m$,
$CH_2CH_2CH_2(-OCH_2CH_2)_m OCH_2CH_2CH_2$
$CH_2CH_2(-OCH_2CH_2)_m OCH_2CH_2$,
$CH_2CH_2CH_2CH_2(-OCH_2CH_2CH_2CH_2)_m$,
$CH_2C(CH_3)H(-OCH_2C(CH_3)H)_m$ or
$CH_2CH_2CH_2(-OCH_2CH_2CH_2CH_2)_m OCH_2CH_2CH_2$,
where m=0–7,
and
$R^1,R^2$=H and/or $CH_2OH$.

This invention accordingly provides bridged, if approriate methylolated bis-4,5-dihydroxyimidazolidin-2-ones of the formula 1, a two-stage process for their preparation, a one-stage process for preparing the bridged methylolated bis-4,5-dihydroxyimidazolidin-2-ones of the formula 1, including the compound where $X=(CH_2)_6$, and generally also for the use of these bridged methylolated bis-4,5-dihydroxyimidazolidin-2-ones, including those where $X=(CH_2)_6$, in textile finishing.

Fabrics treated in this way are preferred because of their enhanced tensile strength in particular.

Surprisingly, the formaldehyde content on the fabric is distinctly lower than expected.

The novel process for preparing the bridged, if appropriate methylolated bis-4,5-dihydroxyimidazolidin-2-ones has a two-stage and a one-stage version.

The two-stage version is described in the below-presented chemical reaction equations:

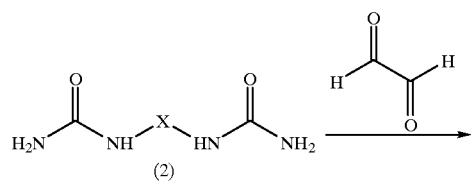

(2)

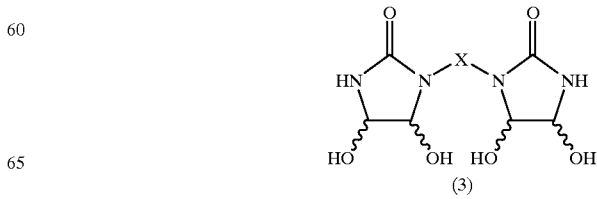

(3)

-continued

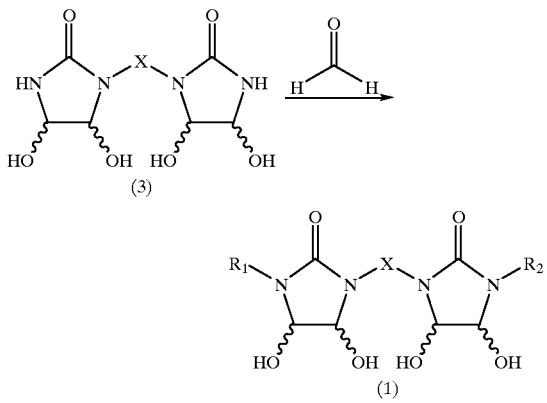

with $R^1$, $R^2$=H and/or $CH_2OH$.

The bridged ureas of the above-presented formula (2) are reacted with glyoxal at from 30° C. to 70° C. in the presence of bases, acids or salts thereof to prepare the compounds of the formula (3). This reaction is preferably carried out with a pH of from 4 to 8 for the solutions. The compounds of the formula (3) are then reacted with formaldehyde at from 30° C. to 700° C. and at from pH 4 to 9 to form the desired bridged methylolated bis-4,5-dihydroxyimidazolidin-2-ones in the second step of the process.

Surprisingly, the bridged methylolated bis-4,5-dihydroxyimidazolidin-2-ones can alternatively also be prepared directly from the same reagents in a single-step process as per the following equation 2:

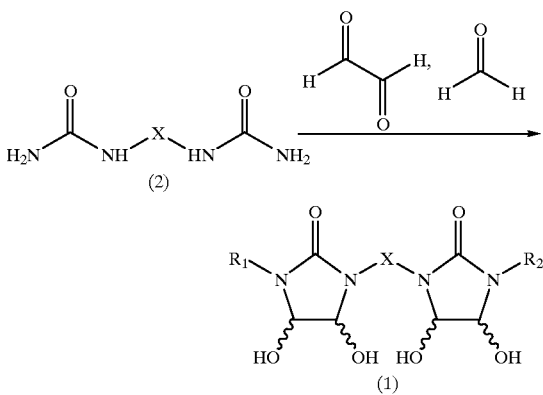

In the direct, single-stage preparation of the bridged methylolated bis-4,5-dihydroxyimidazolidin-2-ones, the starting bridged ureas are preferably reacted with from 1.7 to 2.3, more preferably with from 1.8 to 2.0, mol equivalents of glyoxal and from 1.0 to 2.3, preferably from 1.5 to 2.0, mol equivalents of formaldehyde. The reactions to form the bridged methylolated bis-4,5-dihydroxyimidazolidin-2-ones can be carried out with differently concentrated glyoxal and/or formaldehyde solutions using organic or inorganic acids or bases or buffer substances. The reaction pH is preferably within the range from 4 to 8. The temperature is suitably within the range from 30 to 70° C. Suitable buffer substances are in particular phosphate or acetate buffers.

The Examples which follow illustrate the invention.

PREPARATION EXAMPLES

Example 1

Ethylene-1,2-bis(methylol-4,5-dihydroxyethyleneurea), X=$CH_2CH_2$

A. one-stage synthesis

An initial charge of 0.4 mol of formaldehyde and 0.4 mol of glyoxal was admixed with about 0.2 mol of ethylenebisurea at about pH 5. The mixture was stirred at 50° C. and pH 6–7 for several hours. Once the free aldhyde content indicated a conversion of about 90%, the mixture was filtered. Product weight: 106 g having a water content of 52%.

$^{13}$C—NMR (enantiomer mixture) ($D_2O$) $\delta$(ppm)=40.8, 41.8 ($NCH_2$), 66.7, 66.8 ($NCH_2OH$), 79.5, 80.4, 81.4, 84.6, 86.3, 87.0, 87.6 (CHOH), 161.1, 161.2 (CO); IR (cm$^{-1}$)= 3500–3200 (broad O—H), 2950 (m, C—H), 1697 (s, C=O), 1487 (s), 1326 (m), 1246 (s), 1030 (s).

The strong ethylenediurea signals at 1653 and 1604 cm$^{-1}$ had disappeared.

B. two-stage syntheis

An initial charge of 0.4 mol of glyoxal was adjusted to pH 5.4 with sodium acetate and then admixed with 0.2 mol of ethylenebisurea. After 5 hours at 40° C. 0.29 mol of formaldehyde was added, the pH was adjusted to 6 and the mixture was stirred at 50° C. for several hours. Once the aldehyde content had indicated a conversion of about 90%, the reaction was ended. Product weight: 98 g having a water content of 52%.

Example 2

Propylene-1,3-bis(N-methylol-4,5-dihydroxyethyleneurea), X=$CH_2CH_2CH_2$

A. one-stage synthesis

A solution of 0.4 mol of formaldehyde with 0.4 mol of glyoxal was adjusted to about pH 5.5 with a phosphate buffer. After addition of 0.2 mol of propylenebisurea, the mixture was heated to 50° C., adjusted to pH 6–6.5 and stirred for several hours until the conversion was greater than 90%. Product weight: 110 g having a water content of 46%.

$^{13}$C—NMR (enantiomer mixture) ($D_2O$) $\delta$(ppm)=26.4, 26.6 ($CH_2$), 37.3, 37.6 ($NCH_2$), 62.5, 63.0 ($NCH_2OH$), 75.8, 77.5, 82.6, 84.3, 84.4 (cycl. CHOH), 156.7, 157.0 (CO); IR(cm$^{-1}$)=3500–3200 (broad O—H), 2944 (m, C—H), 1697 (s, C=O), 1487 (s), 1246 (s), 1030 (s).

The strong propylenediurea signals at 1647, 1598 and 1555 cm$^{-1}$ had disappeared.

B. two-stage synthesis

An initial charge of 0.4 mol of glyoxal was adjusted to pH 1.4 with sulfuric acid and then admixed with 0.2 mol of propylenebisurea. The stirability was increased if necessary by the addition of water. After 24 hours at 40° C., 0.29 mol of formaldehyde was added, the pH was adjusted to 6 with sodium acetate, and the mixture was stirred at 50° C. for several hours. Once the aldehyde content indicated a conversion of about 90%, the mixture was filtered. Product weight: 103 g having a water content of 57%.

Example 3

Hexamethylene-1,6-bis(N-methylol-4,5-dihydroxyethyleneurea), X= $CH_2CH_2CH_2CH_2CH_2CH_2$ A solution of 0.58 mol of formaldehyde and 0.6 mol of glyoxal was adjusted to about pH 5.4 with sodium hydroxide solution and then diluted with 50 ml of water. After addition of 0.3 mol of hexamethylenebisurea, the mixture was heated to 55° C., and adjusted to pH 6–7 and stirred for several hours until the conversion was greater than 90%; it was then filtered. Product weight: 250 g having a water content of 57%. The water content was adjusted to 30% by concentrating at about 20 Torr.

$^{13}C$—NMR (enantiomer mixture) (D$_2$O) δ(ppm)=28.2, 29.7, 42.5 (CH$_2$), 66.6 (NCH$_2$OH), 79.3, 80.4, 86.0, 87.0 (CHOH), 161.0 (CO); IR(cm$^{-1}$)=3500–3200 (broad O—H), 2938 (m, C—H), 2864 (m, C—H), 1697 (s, C=O), 1493 (s), 1246 (s), 1030 (s).

The strong hexamethylenediurea signals at 1654, 1598 and 1561 cm$^{-1}$ had disappeared.

Example 4

Cyclohexamethylene-1,4-bis(N-methylol-4,5-dihydroxyethyleneurea), X=cyclohexyl

A solution of 0.4 mol of formaldehyde and 0.4 mol of glyoxal was adjusted to about pH 5.4 with sodium hydroxide solution. After addition of 0.2 mol of cyclohexylbisurea, the mixture was gradually heated to 50° C., adjusted to pH 6–7 and stirred for several hours until the aldehyde conversion was greater than 90%, and then filtered. Product weight: 112 g of the suspension having a water content of 41%.

IR(cm$^{-1}$)=3500–3200 (broad O—H), 2950 (m, C—H), 2858 (m, C—H), 1690 (s, C=O), 1690 (s, C=O), 1487 (s), 1265 (m), 1079 (m) 1030 (m).

The strong hexamethylenediurea signals at 1660, 1598 and 1549 cm$^{-1}$ had disappeared.

Example 5

2,2-Dimethylpropylene-1,3-bis(N-methylol-4,5-dihydroxy-ethyleneurea), X=CH$_2$C(CH$_3$)$_2$CH$_2$ Preparation similar to Example 4.

$^{13}C$—NMR (enantiomer mixture) (D$_2$O) δ(ppm)=25.7, 26.0, 26.5 (CH$_3$), 40.9, 40.9, 41.2 (C), 50.4, 50.7, 51.0, 51.2 (NCH$_2$), 66.3, 66.8 (CH$_2$OH), 79.3, 82.3, 85.6, 88,2 (CHOH), 162.0, 162, 2 (CO); IR(cm$^{-1}$)=3500–3200 (broad O—H), 2963 (m, C—H), 1684 (s, C=O), 1486 (s), 1258 (m), 1036 (m).

The strong 2,2-dimethylpropylenediurea signals at 1604, 1579 and 1561 cm$^{-1}$ had disappeared.

Example 6

2-Hydroxypropylene-1,3-bis(N-methylol-4,5-dihydroxy-ethyleneurea), X=CH$_2$CH(OH)CH$_2$ Preparation similar to Example 4, but with 0.05% of phosphate.

$^{13}C$—NMR (enantiomer mixture) (DMSO) δ(ppm)=43.8, 43.9, 44.1 (NCH$_2$), 62.6, 62.9, 63.0 (CH$_2$OH), 66.5, 66.7, 67.3, 67.5, 68.6 (CHOH), 75.8, 77.9, 78.0, 78.5, 81.8, 82.5, 84.6, 85.3, 85.4 (cycl. CHOH), 156.7, 156.8, 156.9 (CO); IR(cm$^{-1}$)=3500–3200 (broad O—H), 2944 (m, C—H), 1691 (s, C=O), 1493 (s), 1252 (m), 1024 (m).

The strong 2-hydroxypropylenediurea signals at 1629 and 1579 cm$^{-1}$ had disappeared.

Example 7

3,6-Dioxaoctan-1,8-bis(N-methylol-4,5-dihydroxyethyleneurea), X=CH$_2$CH$_2$OCH$_2$CH$_2$OCH$_2$CH$_2$ Preparation similar to Example 4.

Example 8

4-Oxaheptane-1,7-bis(N-methylol-4,5-dihydroxyethyleneurea), X=CH$_2$CH$_2$CH$_2$OCH$_2$CH$_2$CH$_2$ An initial charge of 0.4 mol of formaldehyde and 0.4 mol of glyoxal was admixed with 0.2 mol of 4-oxaheptane-1,7-bisurea at about pH 5.2. The reaction solution was diluted with 1.2 mol of water. It was then stirred at 50° C. and pH 6.3–6.5 for 24 hours. After filtering, the product had a water content of 50.5%.

$^{13}C$—NMR (enantiomer mixture) (D$_2$O) δ(ppm)=30.0, 30.2 (CH$_2$), 40.0, 40.1 (NCH$_2$), 66.5, 66.6, 66.7 (CH$_2$OH), 70.7, 70.8 (CH$_2$OR), 79.4, 80.8, 86.1, 87.2 (cycl. CHOH), 161.1, 161.3 (CO); IR(cm$^{-1}$)=3500–3200 (broad O—H), 2956 (m, C—H), 2870 (m, C—H), 1690 (s, C=O), 1493 (s), 1252 (m), 1024 (m).

The strong 3,6-dioxaoctane-1,8-diurea signals at 1654, 1604 and 1570 cm$^{-1}$ had disappeared.

Example 9

4,7-Dioxadecane-1,10-bis(N-methylol-4,5-dihydroxyethyleneurea), X=CH$_2$CH$_2$CH$_2$OCH$_2$CH$_2$OCH$_2$CH$_2$CH$_2$ Preparation similar to Example 4.

IR(cm$^{-1}$)=3500–3200 (broad O—H), 2950 (m, C—H), 2876 (m, C—H), 1678 (s, C=O), 1493 (s), 1246 (m), 1085 (m), 1023 (m).

The strong 4,7-dioxadecane-1,10-diurea signals at 1654 and 1567 cm$^{-1}$ had disappeared.

Example 10

4,9-Dioxadodecane-1,12-bis(N-methylol-4,5-dihydroxy-ethyleneurea), X=CH$_2$CH$_2$CH$_2$—OCH$_2$CH$_2$CH$_2$CH$_2$—OCH$_2$CH$_2$CH$_2$ Preparation similar to Example 4.

$^{13}C$—NMR (enantiomer mixture) (D$_2$O) δ(ppm)=27.9 (CH$_2$), 29.8, 30.0 (CH$_2$), 39.7, 39.9 (CH$_2$), 66.6, 66.4, (OCH$_2$), 70.2, 70.4 (OCH$_2$), 72.9, (OCH$_2$), 79.1, 80.5, 85.8, 87.0 (cycl. CHOH), 160.7, 160.9 (CO); IR(cm$^{-1}$)=3500–3200 (broad O—H), 2950 (m, C—H), 2870 (m, C—H), 1697 (s, C=O), 1499 (s), 1258 (m), 1116 (m), 1023 (m).

The strong 4,9-dioxadodecane-1,12-diurea signals at 1666 and 1567 cm$^{-1}$ had disappeared.

Application Testing:

a) Treatment of Test Fabrics:

The products were used to prepare a 4% strength solution (based on 100% solids) additionally comprising 1.2% of magnesium chloride crystals as catalyst. The test fabric (cotton) was padded with these solutions to a wet pickup of 75%. It was then dried at 120° C. to a residual moisture content of 6–8%. Curing took place at 150° C. over 4 min.

|  | 0 | DMDHEU | Ex. 3 | Ex. 5 | Ex. 6 | Ex. 7 | Ex. 8 | Ex. 10 |
|---|---|---|---|---|---|---|---|---|
| Dry crease recovery angle°, W + F | 135 | 227 | 214 | 218 | 213 | 208 | 214 | 204 |
| Tensile strength, N (40 × 100) | 335 | 243 | 251 | 277 | 255 | 302 | 318 | 269 |
| Formaldehyde (ppm): | | | | | | | | |
| Shirley I | 12 | 542 | 161 | 266 | 365 | 298 | 263 | 125 |
| AATCC 112 | 6 | 819 | 246 | 356 | 549 | 350 | 472 | 254 |
| LAW 112 | 2 | 596 | 242 | 343 | 402 | 277 | 348 | 257 |

We claim:

1. A bridged bis-4,5-dihydroxyimidazolidin-2-one compound having the formula (1):

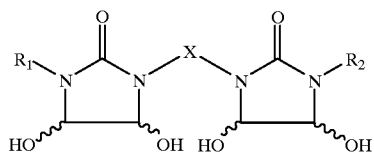

(1)

where X is $(CH_2)_n$, where n is 2, 3, 4, 5, 7, 8, 9 or 10, branched or cyclic alkyl, each with or without one or more heteroatoms in the alkyl chain, having at most 42 atoms, including the heteroatoms, in the alkyl chain,
$CH_2CH_2(-OCH_2CH_2)_m$,
$CH_2CH_2CH_2(-OCH_2CH_2CH_2)_m$,
$CH_2CH_2CH_2(-OCH_2CH_2)_mOCH_2CH_2CH_2$,
$CH_2CH_2(-OCH_2CH_2CH_2)_mOCH_2CH_2$,
$CH_2CH_2CH_2CH_2(-OCH_2CH_2CH_2CH_2)_m$,
$CH_2C(CH_3)H(-OCH_2C(CH_3)H)_m$ or
$CH_2CH_2CH_2(-OCH_2CH_2CH_2CH_2)_mOCH_2CH_2CH_2$,
where m is 0–7,
and
$R^1$ and $R^2$ is each independently H or $CH_2OH$.

2. The bridged compound of claim 1, wherein a heteroatom in the alkyl chain is selected from the group consisting of O, S, N and P.

3. A process for preparing the bridged bis-4,5-dihydroxyimidazolidin-2-one compound of claim 1, which comprises in a first step reacting a bridged urea compound of the formula (2):

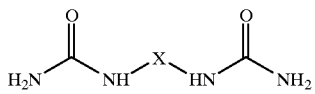

(2)

where X is $(CH_2)_n$, where n is 2, 3, 4, 5, 7, 8, 9 or 10, branched or cyclic alkyl, each with or without one or more heteroatoms in the alkyl chain, having at most 42 atoms, including the heteroatoms, in the alkyl chain,
$CH_2CH_2(-OCH_2CH_2)_m$,
$CH_2CH_2CH_2(-OCH_2CH_2CH_2)_m$,
$CH_2CH_2CH_2(-OCH_2CH_2)_mOCH_2CH_2CH_2$,
$CH_2CH_2(-OCH_2CH_2CH_2)_mOCH_2CH_2$,
$CH_2CH_2CH_2CH_2(-OCH_2CH_2CH_2CH_2)_m$,
$CH_2C(CH_3)H(-OCH_2C(CH_3)H)_m$ or
$CH_2CH_2CH_2(-OCH_2CH_2CH_2CH_2)_mOCH_2CH_2CH_2$,
where m is 0–7, with glyoxal at from about 30° to 70° C. and then, in a second step, to obtain a compound wherein at least one of $R^1$ and $R^2$ is $CH_2OH$, reacting the resulting product with formaldehyde at from about 30 to 70° C.

4. The process as claimed in claim 3, wherein the reaction with the glyoxal is conducted at from about pH 4 to 8 and the reaction with formaldehyde is conducted at from about pH 4 to 9.

5. A process for preparing a bis-4,5-dihydroxyimidazolidin-2-one compound having the formula (1a):

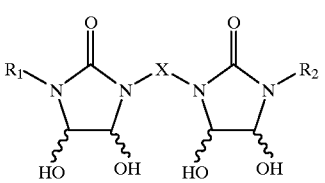

(1a)

where X is $(CH_2)_n$, where n is 2, 3, 4, 5, 6, 7, 8, 9 or 10, branched or cyclic alkyl, each with or without one or more heteroatoms in the alkyl chain, having at most 42 atoms including heteroatoms in the alkyl chain
$CH_2CH_2(-OCH_2CH_2)_m$,
$CH_2CH_2CH_2(-OCH_2CH_2CH_2)_m$,
$CH_2CH_2CH_2(-OCH_2CH_2)_mOCH_2CH_2CH_2$,
$CH_2CH_2(-OCH_2CH_2CH_2)_mOCH_2CH_2$,
$CH_2CH_2CH_2CH_2(-OCH_2CH_2CH_2CH_2)_m$,
$CH_2C(CH_3)H(-OCH_2C(CH_3)H)_m$ or
$CH_2CH_2CH_2(-OCH_2CH_2CH_2CH_2)_mOCH_2CH_2CH_2$,
where m is 0–7,
and $R^1$ and $R^2$ is each independently H or $CH_2OH$ and at least one $R^1$ and $R^2$ is $CH_2OH$ which comprises reacting a bridged urea compound conforming to the formula (2):

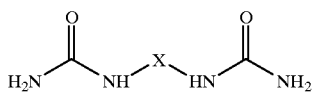

(2)

where X is as defined above,
with glyoxal and formaldehyde at from about 30° C. to 70° C. and at a pH of from about 4 to 9 in a single step.

6. The process as claimed in claim 5, wherein the bridged urea compound of the formula (2) is reacted with from about 1.7 to 2.3 mol equivalents of glyoxal and from about 1 to 2.3 mol equivalents of formaldehyde.

7. A method of crosslinking textiles, which comprises effecting said crosslinking with a bridged bis-4,5-dihydroxyimidazolidin-2-one, of the formula (1a):

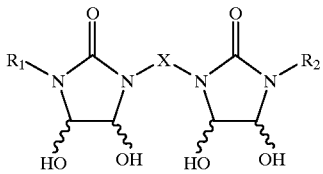

(1a)

where X is $(CH_2)_n$, where n is 2, 3, 4, 5, 6 7, 8, 9 or 10, branched or cyclic alkyl, each with or without one or more heteroatoms in the alkyl chain, having at most 42 atoms, including the heteroatoms, in the alkyl chain, $CH_2CH_2(—OCH_2CH_2)_m$,
$CH_2CH_2CH_2(—OCH_2CH_2CH_2)_m$,
$CH_2CH_2CH_2(—OCH_2CH_2)_mOCH_2CH_2CH_2$,
$CH_2CH_2(—OCH_2CH_2CH_2)_mOCH_2CH_2$,
$CH_2CH_2CH_2CH_2(—OCH_2CH_2CH_2CH_2)_m$,
$CH_2C(CH_3)H(—OCH_2C(CH_3)H)_m$ or
$CH_2CH_2CH_2(—OCH_2CH_2CH_2CH_2)_mOCH_2CH_2CH_2$,
where m is 0–7, and $R^1$ and $R^2$ is each independently H or $CH_2OH$ in order to finish said textiles.

8. The method of claim 7, wherein in said compound of the formula (1a), a heteroatom in the alkyl chain is selected from the group consisting of O, S, N and P.

9. A compound of claim 1, wherein at least one of $R^1$ and $R^2$ is $CH_2OH$.

10. A process according to claim 3, wherein at least one of $R^1$ and $R^2$ is $CH_2OH$ and the second step is carried out.

11. The method of claim 7, wherein at least one of $R^1$ and $R^2$ is $CH_2OH$.

* * * * *